(12) United States Patent
Blessing

(10) Patent No.: US 11,768,176 B2
(45) Date of Patent: Sep. 26, 2023

(54) ION SOURCE WITH GAS DELIVERY FOR HIGH-FIDELITY ANALYSIS

(71) Applicant: MKS Instruments, Inc., Andover, MA (US)

(72) Inventor: James Edward Blessing, Morgan Hill, CA (US)

(73) Assignee: MKS Instruments, Inc., Andover, MA (US)

( * ) Notice: Subject to any disclaimer, the term of this patent is extended or adjusted under 35 U.S.C. 154(b) by 0 days.

(21) Appl. No.: 17/647,239

(22) Filed: Jan. 6, 2022

(65) Prior Publication Data

US 2023/0213479 A1    Jul. 6, 2023

(51) Int. Cl.
| | |
|---|---|
| *G01N 27/64* | (2006.01) |
| *H01J 49/14* | (2006.01) |
| *H01J 49/24* | (2006.01) |
| *H01J 49/42* | (2006.01) |
| *G01N 33/00* | (2006.01) |
| *H01J 49/00* | (2006.01) |

(52) U.S. Cl.
CPC ......... *G01N 27/64* (2013.01); *G01N 33/0027* (2013.01); *H01J 49/0031* (2013.01); *H01J 49/14* (2013.01); *H01J 49/147* (2013.01); *H01J 49/24* (2013.01); *H01J 49/42* (2013.01)

(58) Field of Classification Search
CPC . G01N 27/64; G01N 33/0027; H01J 49/0031; H01J 49/14; H01J 49/24; H01J 49/42; H01J 49/147
USPC ........................................................ 250/288
See application file for complete search history.

(56) References Cited

U.S. PATENT DOCUMENTS

| | | | |
|---|---|---|---|
| 4,018,241 | A | 4/1977 | Sodal et al. |
| 4,658,143 | A | 4/1987 | Tokiguchi et al. |
| 4,794,252 | A | 12/1988 | Bateman et al. |
| 9,305,759 | B2 | 4/2016 | McEwen et al. |
| 10,541,122 | B2 | 1/2020 | Blessing et al. |
| 11,581,172 | B2 * | 2/2023 | Ueno .................. H01J 49/0031 |

(Continued)

FOREIGN PATENT DOCUMENTS

EP        0252758 A2    1/1988

OTHER PUBLICATIONS

International Search Report and Written Opinion received for PCT Patent Application No. PCT/US2022/082107, dated Apr. 17, 2023, 16 pages.

(Continued)

*Primary Examiner* — Kiet T Nguyen
(74) *Attorney, Agent, or Firm* — Hamilton, Brook, Smith & Reynolds, P.C.

(57) ABSTRACT

In a system for processing gas, a gas analyzer in a gas analyzer chamber measures a quantity of ions generated from a gas. An ionization source includes an ionization chamber and an electron source for generating ions for the gas analyzer. The ionization chamber encompasses an ionization region in which particles of the gas are charged to form the ions. A channel directs the gas from a gas source into the ionization chamber, and the channel extends to a surface of the ionization chamber. An ionization source vacuum pump is in gaseous communication with the ionization chamber via a substantially large opening, and operates to draw gas from the ionization chamber.

23 Claims, 13 Drawing Sheets

(56) References Cited

U.S. PATENT DOCUMENTS

| | | | |
|---|---|---|---|
| 2001/0048074 A1* | 12/2001 | Shiokawa | H01J 49/145 |
| | | | 250/286 |
| 2002/0036263 A1 | 3/2002 | Shiokawa et al. | |
| 2015/0144779 A1 | 5/2015 | Verenchikov | |
| 2016/0247669 A1 | 8/2016 | Tateishi et al. | |

OTHER PUBLICATIONS

Ma, Y., et al., "High Sensitivity Mass Spectrometer System For Contaminant Measurement In High Purity Gases", Review of Scientific Instruments, vol. 67, No. 10, 1996, pp. 3465-3471.

* cited by examiner

ION SOURCE WITH GAS DELIVERY FOR HIGH-FIDELITY ANALYSIS

BACKGROUND

There are various uses for extremely high purity gases, which can be difficult to produce, maintain and deliver. This creates a need for gas purity analysis, extending to extremely low levels of impurities of many types. Mass spectrometry can be a good analytical method, capable of detecting nearly any gaseous contaminant, but there are several limitations to achieving extremely low levels of impurity detection. Sources of such gases are generally at relatively high pressure (i.e., 1 bar or greater).

A quadrupole mass analyzer (QMA) is a type of mass spectrometer that is commonly used to analyze a gas to ensure a desired gas composition, including levels of impurities. Analyzing a gas from a high pressure (e.g., greater than 1E-4 Torr) requires sampling the gas in a high vacuum chamber where it is ionized and analyzed. Because the vacuum is not perfect, residual gases are added to the sample gas, limiting detection of low amounts of gas species matching those residual gases. Closed Ion Sources (CISs) create a stage of relatively high pressure where gas ionization takes place, raising the ratio of sample gas to background gas. However, this method is insufficient for very low trace impurity monitoring for many common contaminants, such as $H_2$, $H_2O$, $N_2$, CO, $O_2$ and $CO_2$.

SUMMARY

Example embodiments include a system for processing and analyzing gas. A gas analyzer in a gas analyzer chamber may be configured to measure a quantity of ions generated from a gas. A gas analyzer vacuum pump may be configured to evacuate the gas analyzer chamber. An ionization source may include an ionization chamber and an electron source. The ionization chamber may encompass an ionization region in which particles of the gas are charged to form the ions, including 1) an aperture permitting passage of the ions between the ionization chamber and the gas analyzer chamber, 2) an opening substantially larger than the aperture and positioned away from the aperture, and 3) a perforation through the chamber, at a position between the aperture and the opening, for electrons to enter the ionization region. The electron source may be configured to direct electrons into the ionization chamber via the perforation and through the gas in the ionization chamber into the ionization region to ionize the gas. A channel may be configured to direct the gas from a gas source into the ionization chamber, and the channel may extend to a surface of the ionization chamber (e.g., terminating at the surface or extending through the surface). An ionization source vacuum pump may be in gaseous communication with the ionization chamber via the opening, and may be configured to draw gas from the ionization chamber.

The gas analyzer may be removeable axially from the gas analyzer chamber. The channel may extend axially beside the gas analyzer and may be removed axially with the gas analyzer and the ionization chamber. The channel may extend to the surface of the ionization chamber at a location from the perforation to the aperture. The aperture and the opening may be located at opposite ends of the ionization chamber. The channel may be adapted to direct at least a portion of the gas into the ionization region prior to collision with an interior surface of the ionization chamber.

The channel may include a terminal segment that is oriented towards the ionization region. The terminal segment may extend into the ionization chamber to a location adjacent to an electron stream from the electron source. The ionization chamber may be configured to maintain a gas pressure higher than a gas pressure of the gas analyzer chamber. The ionization chamber may be configured to contain the gas at a pressure below $5 \times 10^{-2}$ Torr, and the gas analyzer chamber may be configured to contain the gas at a pressure below $1 \times 10^{-4}$ Torr. The channel may extend to the surface of the ionization chamber at a location between the perforation for the electrons and the aperture. The gas analyzer may be a quadrupole mass analyzer (QMA).

Further embodiments include a system for processing and analyzing gas, comprising an ionization source and an ionization source vacuum pump. The ionization source may include an ionization chamber, a channel, and an electron source. The ionization chamber may encompass an ionization region in which particles of the gas are charged to form the ions, including 1) an aperture permitting passage of the ions from the ionization chamber to an evacuated gas analyzer chamber and 2) an opening substantially larger than the aperture and positioned away from the aperture, and 3) a perforation through the chamber, at a position between the aperture and the opening, for electrons to enter the ionization region. The channel may be configured to direct the gas from a gas source to the ionization chamber, the channel extending through a surface of the ionization chamber. The electron source may be configured to direct electrons into the ionization chamber via the perforation and through the gas in the ionization chamber to ionize the gas, the ionization chamber encompassing an ionization region in which particles of the gas form the ions. The ionization source vacuum pump may be in gaseous communication with the ionization chamber via the opening, and may be configured to draw gas from the ionization chamber.

The channel and ionization chamber may be removable axially from the gas analyzer chamber. The channel may extend to the surface of the ionization chamber at a location closer to the aperture than the opening. The aperture and the opening may be located at opposite ends of the ionization chamber. The channel may be adapted to direct at least a portion of the gas into the ionization region prior to collision with an interior surface of the ionization chamber. The channel may include a terminal segment that is oriented towards the ionization region. The terminal segment may extend into the ionization chamber to a location adjacent to an electron stream from the electron source.

Further embodiments include a method of processing/analyzing gas. A gas analyzer chamber may be evacuated via a gas analyzer vacuum pump. Gas may be directed, via a channel, from a gas source to an ionization chamber within the gas analyzer chamber, the channel extending to a surface of the ionization chamber. Electrons may then be directed through the gas in the ionization chamber to ionize the gas, the ionization chamber encompassing an ionization region in which particles of the gas are charged to form the ions. The ions may be caused to pass between the ionization chamber and the gas analyzer chamber via an aperture at the ionization chamber. Gas may then be drawn from the ionization chamber through an opening at the ionization chamber via an ionization source vacuum pump, the opening being substantially larger than the aperture and positioned away from the aperture. A quantity of ions generated from a gas may be measured via a gas analyzer.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

Figure 1:
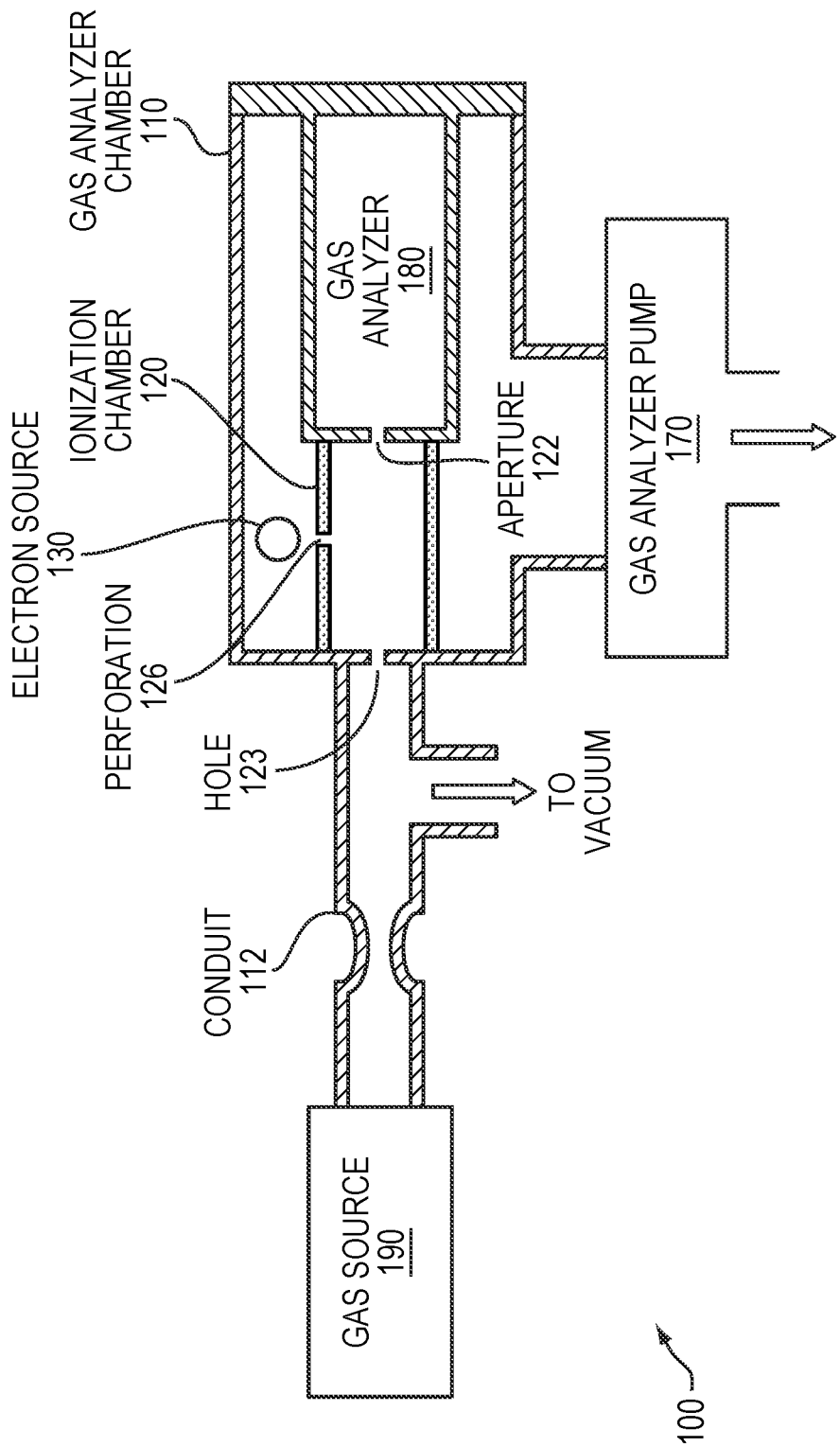
FIG. 1 is a diagram of a gas analyzer assembly in the prior art.

FIG. 1 illustrates a typical system 100 for gas analysis as known in the prior art. A gas source 190 may deliver a gas at a given pressure (e.g., 750 Torr) via a flow-restricting conduit 112 to a source of vacuum. Analyzing a sample gas from a high pressure source (e.g., greater than 1E-4 Torr) requires sampling the gas in a high vacuum chamber where it is ionized and analyzed. To do so, the conduit 112 diverts a portion of the gas to a gas analyzer chamber 110 via a small hole 123, wherein some of the diverted gas is ionized in an ionization chamber 120 and transferred, via an aperture 122, to a gas analyzer 180 (e.g., a quadrupole mass analyzer (QMA)). The gas analyzer 180 is held at a high vacuum, e.g., less than 1E-4 Torr, by a gas analyzer vacuum pump 170. Because the vacuum within the gas analyzer chamber 110 is not perfect, residual gases are added to the sample gas, limiting detection of low amounts of gas species matching those residual gases. A closed ion source (CIS), such as the ionization chamber 120, addresses this problem by creating an intermediate stage of relatively high pressure where gas ionization takes place, raising the sample-to-background gas ratio. In particular, the ionization chamber 120 is closed to the gas analyzer chamber 110 except for the aperture 122 to the gas analyzer 180 and a perforation 126 for passing electrons from an electron source 130 to ionize the gas. As a result, with conductance in and out of the ionization chamber 120 low, the gas is ionized in the ionization chamber 120 at a higher pressure (e.g., about 1×10E-3 Torr) than the pressure of the gas analyzer chamber 110, but with the same level of background gas as in the gas analyzer chamber 110. Ions are drawn electrostatically to the gas analyzer 180 via the aperture 122. However, surface reactions between the gas particles and the walls of the ionization chamber 120 cause the loss of some reactive species in the gas, as well as create unwanted gas particles.

Figure 2:
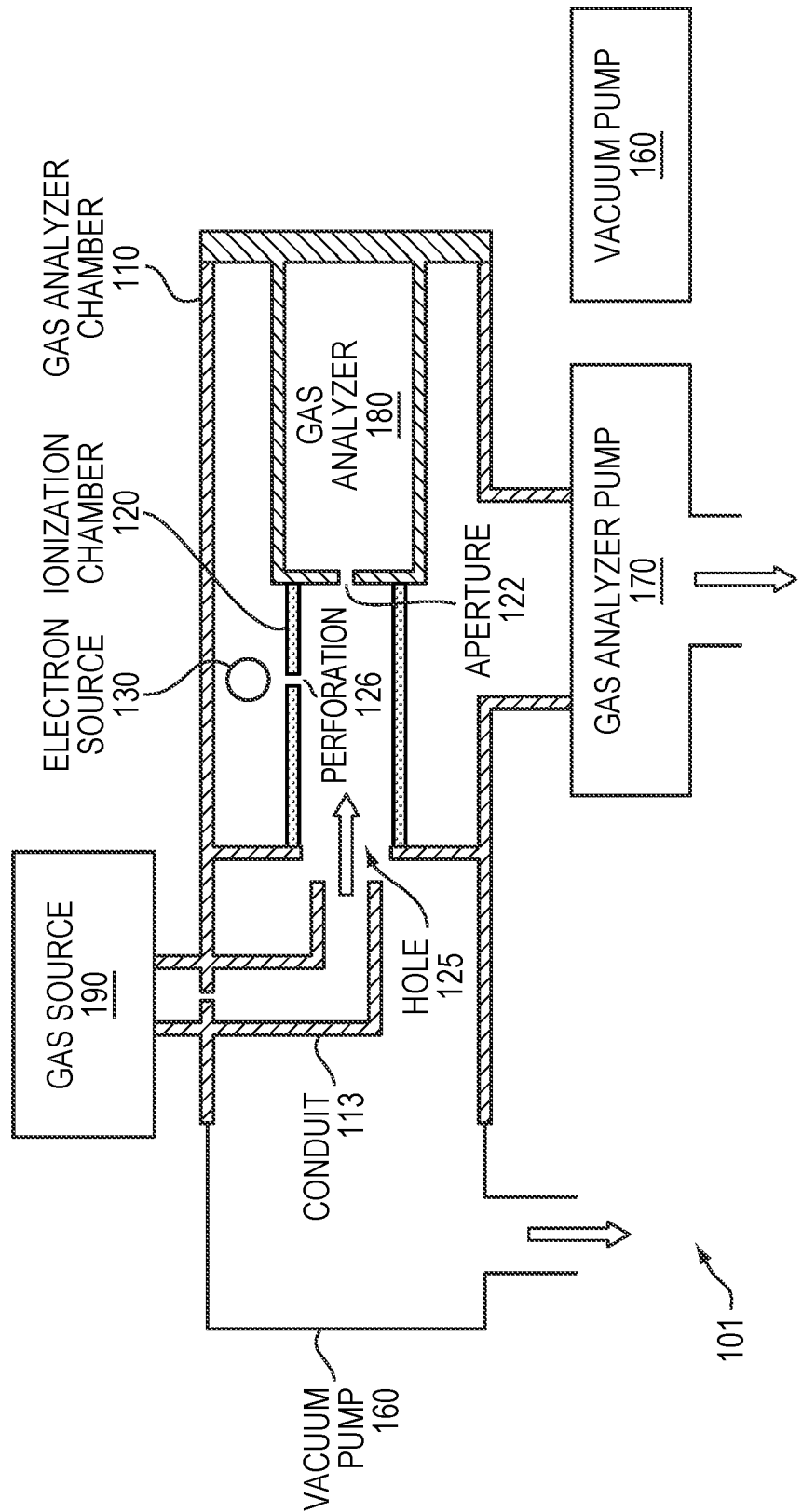
FIG. 2 is a diagram of a further gas analyzer assembly in the prior art.

FIG. 2 illustrates a prior art system 101 for gas analysis in an alternative configuration. To reduce the level of background gas species relative to the system 100, the system 101 provides better conductance from the ionization chamber 120 to a source of very high vacuum (e.g., vacuum pump 160), and provides a higher gas flow to achieve the same pressure at the point of ionization. To do so, a flow-restricting conduit 113 directs gas into a vacuum pump 160 that is connected to the ionization chamber 120 via a large hole 125. The conduit 113, as shown, is oriented to direct a large portion of the gas into the ionization chamber 120 via the hole 125, and the vacuum pump 160 draws the gas toward an outlet. Thus, a large portion of the gas is initially directed into the ionization chamber 120 to provide a higher-pressure volume for ionization before it is evacuated by the vacuum pump 160. Like the system 100, surface reactions still occur between the gas particles and the walls of the ionization chamber 120, causing the loss of some reactive species in the gas, as well as creating unwanted gas particles. Yet in contrast to the system 100, the high rate of gas flow into, and out of, the ionization chamber of the system 101 reduces the relative contributions of those reactions on the concentration of the gas in the ionization chamber 120, and, therefore, on the ions that enter the gas analyzer 180, subsequently.

As a result of the differences over the system 100, the system 101 may achieve a detection limit of certain gas particles that is up to 100× lower than that of the system 100. However, the system 101 still has a number of disadvantages. In particular, the gas flow must enter and exit the ionization chamber 120 through the same hole 125. The added residence time and gas flow reversal in the ionization chamber 120 creates a high number of gas-gas and gas-surface collisions, which results in some loss of reactive species, as well as the creation of by-product species that can interfere accurate measurements of gas by the gas analyzer 180.

Example embodiments, described below, provide a system for processing gas whereby gas may be delivered into a nominally closed ion source for mass spectrometric analysis of gases, particularly ultra-high purity gases, for trace analysis and reduced degradation from surface reactions. Unlike typical closed sources such as shown in FIG. 1, with restricted conductance in and out, such embodiments can provide greater conductance out to a high speed, ultra-high vacuum pump, with a high flow of gas from the mass filter end of the ion source, through the ionization region, and out the high conductance end. Such a configuration optimizes gas pressure at ionization, while minimizing interactions with surfaces and maintains lower pressure in the mass filter and detector.

Figure 3A:
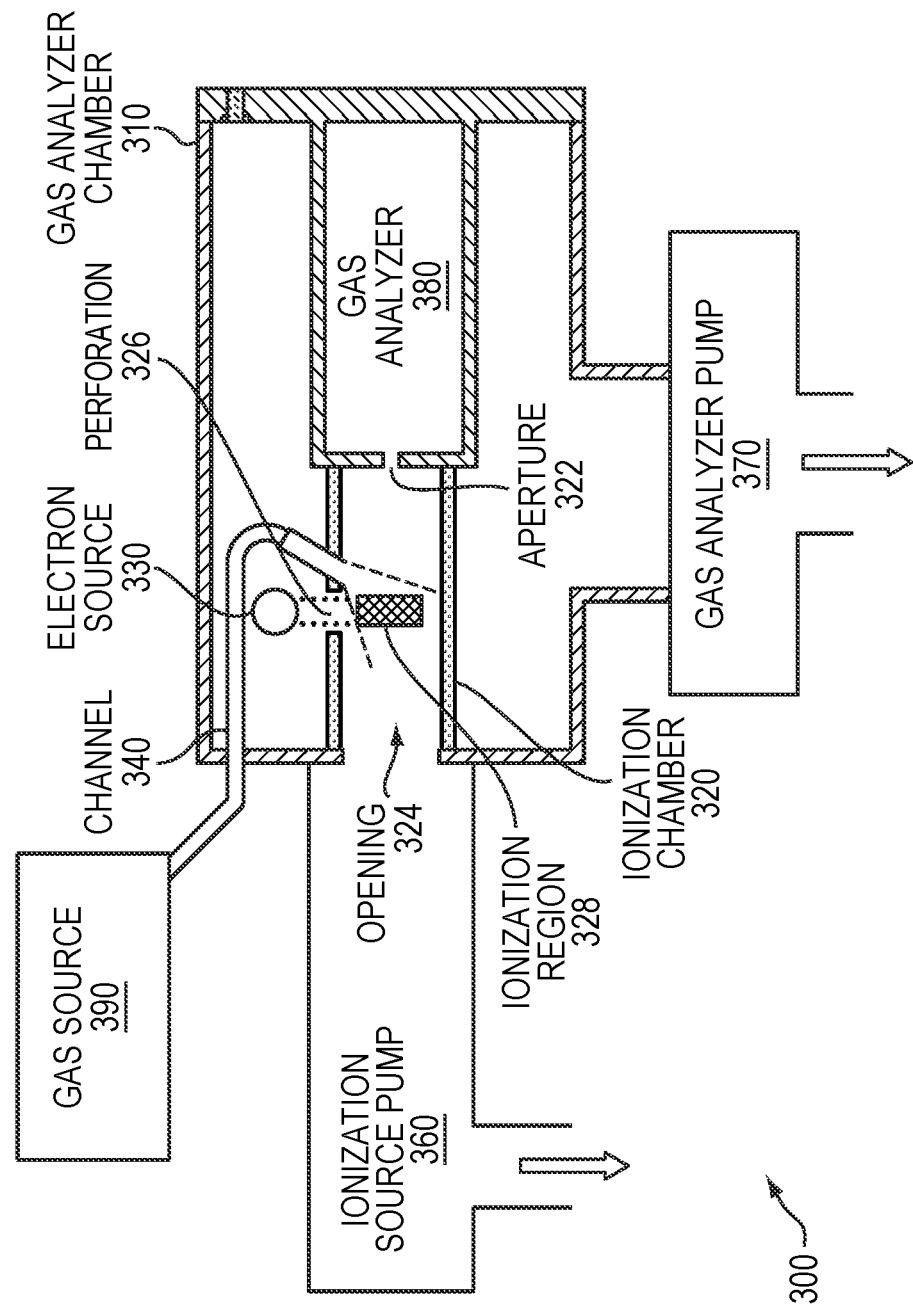
FIGS. 3A-C illustrate gas analyzer systems in example embodiments.

FIG. 3A is a diagram of a gas analyzer system 300 in one embodiment. As shown, a gas analyzer 380 (e.g., a quadrupole mass analyzer (QMA)) in a gas analyzer chamber 310 is configured to measure a quantity of ions generated from a gas. A gas analyzer vacuum pump 370 operates to evacuate the gas analyzer chamber 310, thereby maintaining a high vacuum environment within the chamber 310. An ionization source includes an electron source 330 and an ionization chamber 320. The ionization chamber 320 may include an aperture 322 permitting passage of the ions between the ionization chamber 320 and the gas analyzer chamber 310, an opening 324 substantially larger than the aperture, and a perforation 326 through the chamber, at a position between the aperture 322 and the opening 324, for electrons to enter an ionization region 328.

To generate ions from the gas to be analyzed, the electron source 330 directs electrons via the perforation 326 into the ionization chamber 320, where the electrons charge particles of the gas to form ions largely within an ionization region 328 encompassed by the chamber 320. Ions from the ionization region 328 are drawn into the gas analyzer 380 via the aperture 322, electrostatically. The gas, which originates from a gas source 390, is directed into the ionization chamber 320 via a flow-restricting channel 340. The channel 340 extends to a surface of the chamber 320, and may terminate at the surface of the chamber 320 or may extend through the surface as illustrated in FIG. 5C as described below. The ionization region 328 is a volume in which a large portion of the ionization occurs, which may be due to a greater intersection of the electrons and the gas particles inside the region 328 than outside the region 328. For example, the channel 340 may direct the gas particles toward this region 328 and the electron source 330 may direct electrons toward this region 328. However, due to the expansion of gas particles and electrons within the ionization chamber 320, ionization may also occur within the ionization chamber 320 but outside of the region 328. As shown, the channel 340 may extend to the surface of the ionization chamber 320 at a location closer to the aperture 322 than the opening 324, and the aperture 322 and the opening 324 may be located at opposite ends of the ionization chamber. Further, the channel 340, as shown, may extend to the surface of the ionization chamber 320 at a location between the perforation 326 and the aperture 322. The channel 340, as a result of its orientation and the gas pressure, may be adapted to direct at least a portion of the gas into the ionization region 328 prior to collision with an interior surface of the ionization chamber 320. To facilitate this result, the channel 340 may include a terminal segment that is oriented towards the ionization region 328.

An ionization source pump 360 may be a vacuum pump connected to the gas analyzer chamber 310, and may be in gaseous communication with the ionization chamber 320 via the opening 324. The ionization source pump 360 may be configured to draw the gas from the ionization chamber 320, directing the gas to an exhaust. Thus, the gas may maintain a flow from the gas source 390, through the channel 340, into the ionization chamber 320 where a portion of the gas is ionized in the ionization region 328. The gas that does not enter the gas analyzer 380 or is not evacuated by the gas analyzer vacuum pump 370 may then be drawn from the ionization chamber 320 by the ionization source pump 360. The ionization source pump 360 may be configured and oriented relative to the ionization chamber 320 such that it draws the gas in a direction that causes at least a desired portion of the gas to pass through the ionization region 328. Due to the operation of the gas analyzer vacuum pump 370 and the ionization source pump 360, the ionization chamber 320 may maintain a substantial vacuum (e.g., $1 \times 10E-10$ Torr) absent gas from the gas source 390. As a result, the amount of residual ambient gas that is ionized and enters the gas analyzer 380 is minimized. The ionization chamber 320, as a result of receiving the gas via the channel 340, may therefore maintain a gas pressure higher than a gas pressure of the gas analyzer chamber 310. For example, the ionization chamber 320 may contain the gas at a pressure below $5 \times 10^{-2}$ Torr, and the gas analyzer chamber 310 may contain the gas at a pressure below $1 \times 10^{-4}$ Torr.

Thus, for a gas to be analyzed, the system 300 provides for originating the gas within the ionization chamber 320 and causing it to flow out to the high vacuum provided by the ionization source pump 360. In this way, the flow of the gas can be greater than in the systems 100 and 101 described above, and the pressure of gas at the point of ionization is also higher, thereby reducing the proportion of unwanted residual gas. Due to the relatively greater directivity of gas flow in system 300, collisions between gas particles and surfaces of the ionization chamber 320 may also be lower, thereby reducing the number of reaction products.

As further advantages, the system 300 may enable optimal sample flow through the ion source, with optimal exit conductance to high vacuum, as well as optimal sample gas pressure at the point of ionization, minimal interaction of the sample gas with the inside surfaces of the ion source and reduced gas-gas (and gas-ion) collisions. Taken together, in example embodiments, these advantages can maximize the fidelity of the ions being representative of the gas stream to less than 1 part per billion (ppb).

Figure 3B:
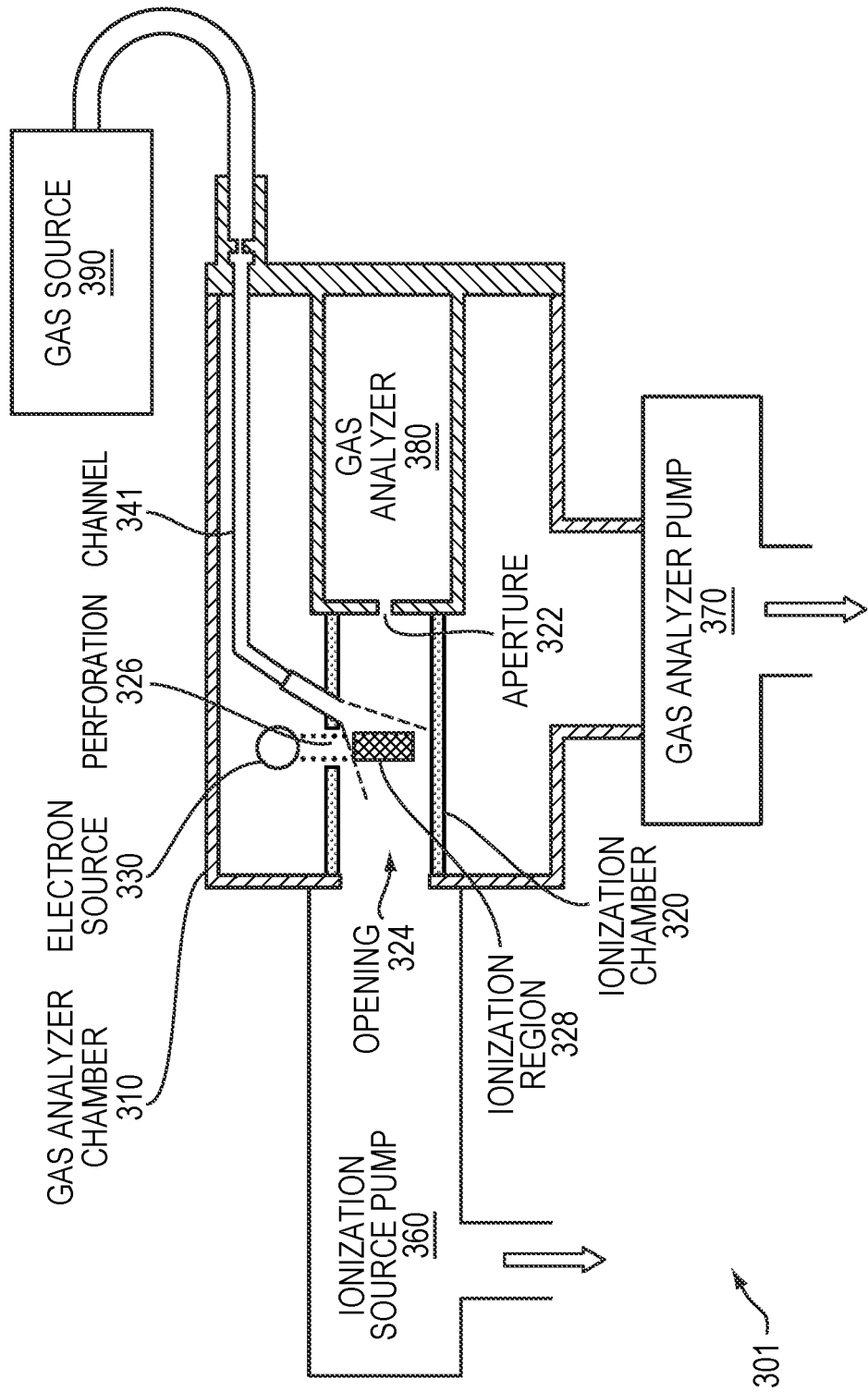

FIG. 3B illustrates a gas analyzer system 301 in a further embodiment. The system 301 may incorporate some or all of the features of the system 300 described above, but may depart from the system 300 in the configuration of a gas channel. In particular, a channel 341 is configured to extend substantially parallel to the upper surface of the gas analyzer 380, and may pass through a right wall of the gas analyzer chamber 310, which may also form a part of an assembly that is removeable from the gas analyzer chamber 310. Further, the channel 341 and related hardware may be configured as part of a common assembly including the ionization chamber 320 and gas analyzer 380, rather than part of the inlet and gas analyzer chamber 310. This configuration permits a precision connection of the channel to be made and maintained with achievable tolerances. The gas delivery path may therefore be integral with the analyzer assembly. Further, the gas analyzer 380 may be removeable axially from the gas analyzer chamber 310. Referring to FIG. 3B, for example, the gas analyzer 380 may be removed by disconnecting it from the gas analyzer chamber 310 and moving it rightward. In this example, the channel 341 extends axially beside the gas analyzer 380 and is removed axially with the gas analyzer 380 and, optionally, the ionization chamber 320. An example of such a connection and disconnection operation is described below with reference to FIGS. 4A-B.

Figure 3C:
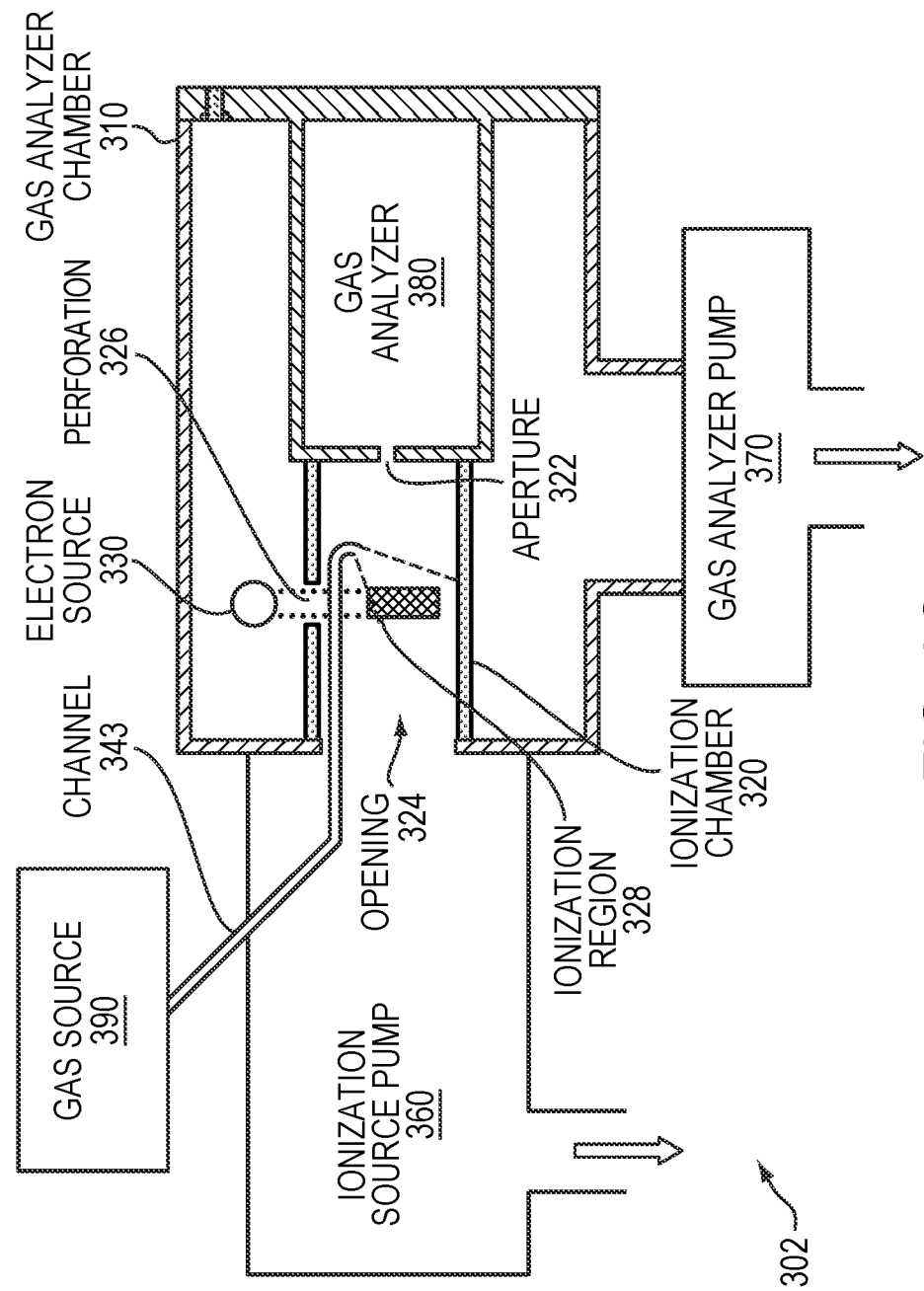

FIG. 3C illustrates a gas analyzer system 302 in a further embodiment. The system 302 may incorporate some or all of the features of the system 300 described above, but may depart from the system 300 in the configuration of a gas channel. In particular, a channel 343 extends through the ionization source pump 360 rather than the gas analyzer chamber 310, and extends into the ionization chamber 320 through the opening 324 rather than through a surface of the ionization chamber 320. A terminal segment of the channel 343 may be located in the ionization chamber at a location closer to the aperture 322 than the opening 324, and may be located between the perforation for the electrons and the aperture, as shown. The terminal segment of the channel 343 may be oriented to direct the gas to collide with the beam of electrons from the electron source 330, thereby creating the ionization region 328 in a location similar to those of the embodiments described above. Further, the channel 343 may be routed away from the perforation 326 so as not to interfere with the beam of electrons, such as is shown in FIG. 6B, described below, where the locations of the perforation 326 and the channel 343 are rotated around the ionization chamber 320 so as not to interfere with each other.

The configuration of the channel 343 can be advantageous in that it does not require the ionization chamber 320 to accommodate a passage for the channel, and it avoids the need for precision alignment between the channel and the ionization chamber 320 during assembly. Further, the assembly containing the gas analyzer 380 does not need to be modified to incorporate the channel 343.

Figure 4A:
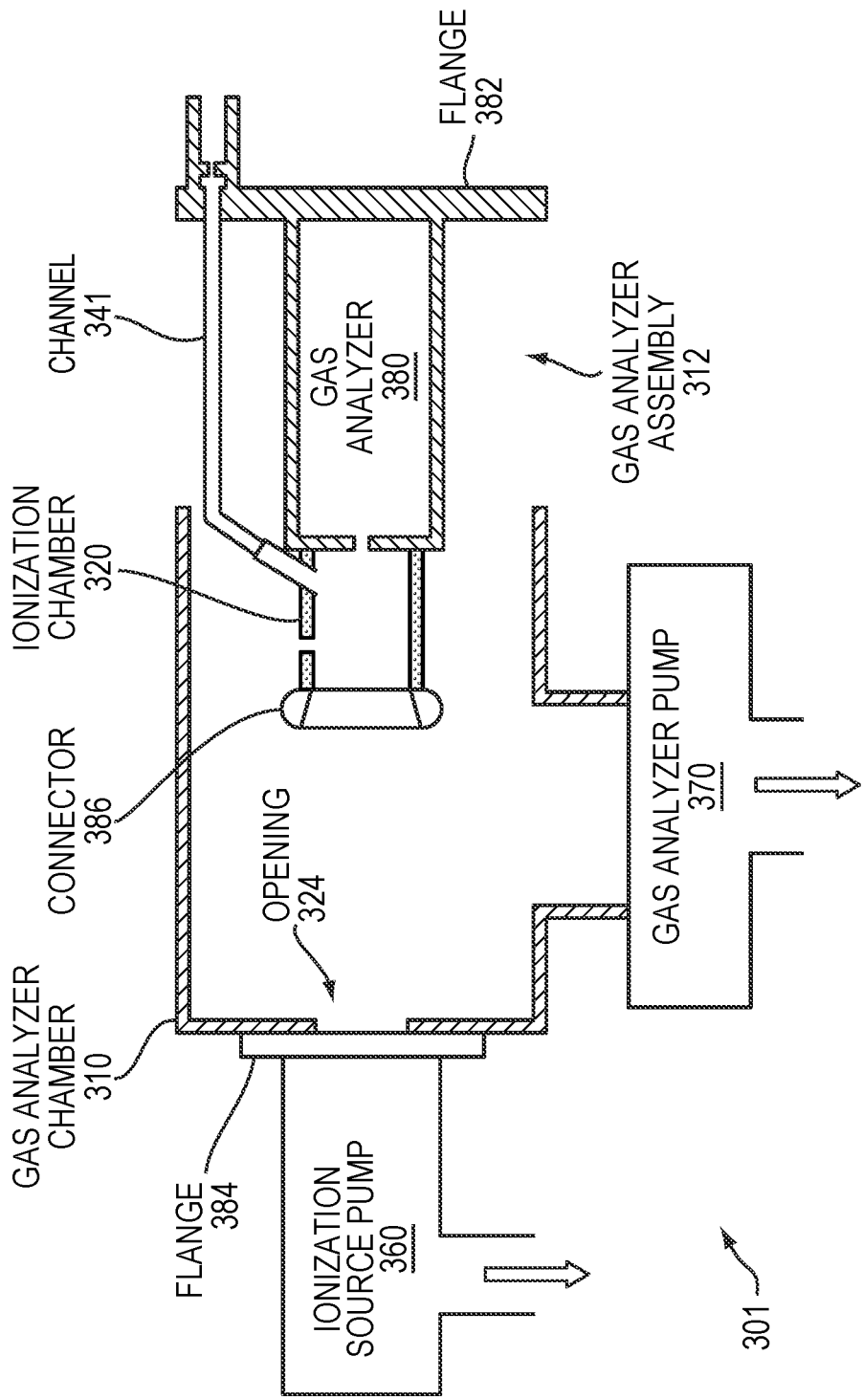
FIGS. 4A-B illustrate assembly of a gas analyzer system in one embodiment.
Figure 4B:
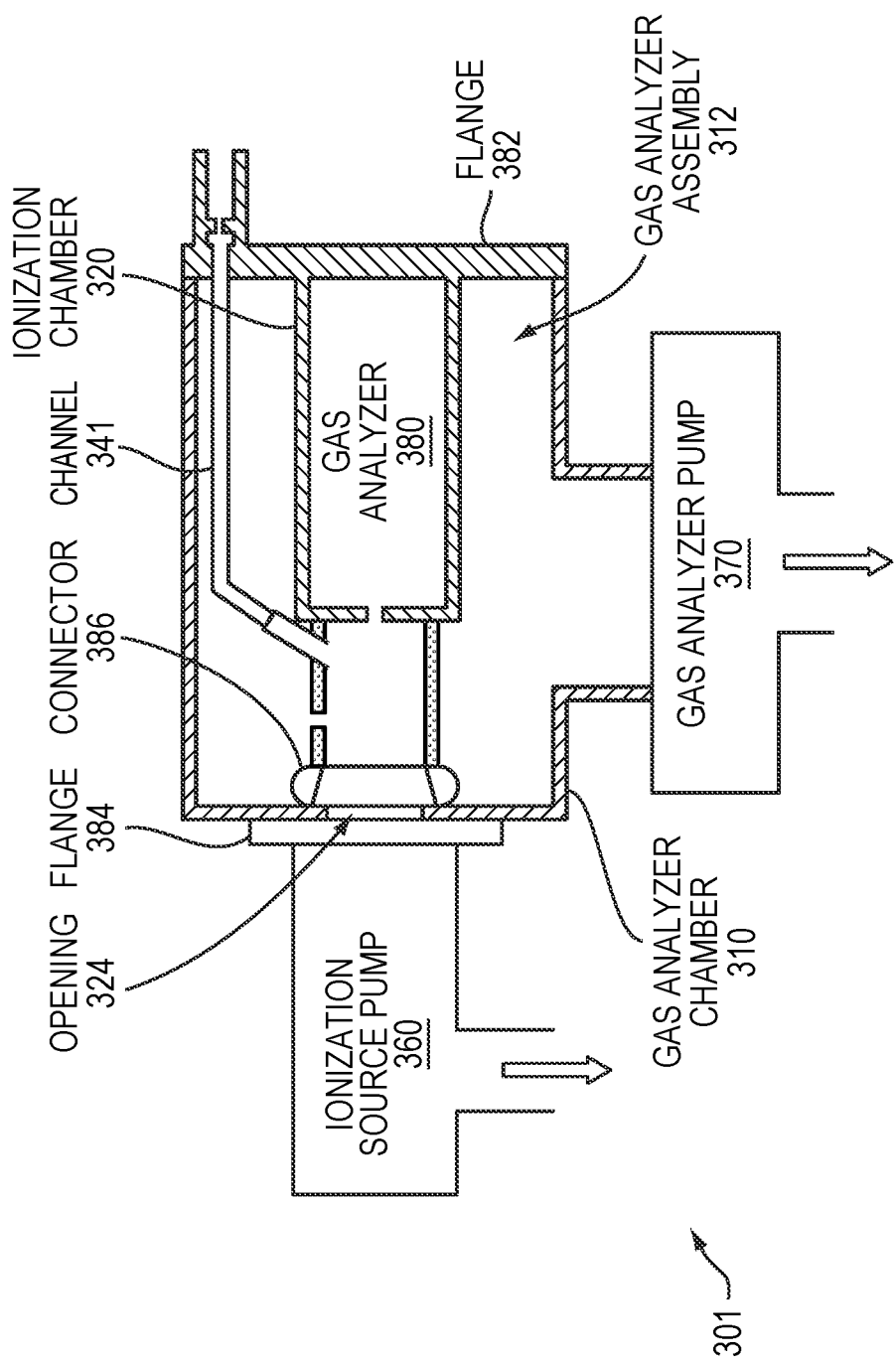

FIGS. 4A-B illustrate an example operation of assembling or disassembling the gas analyzer system 301 of FIG. 3B. For clarity, some elements of FIG. 3B are omitted. In FIG. 4A, the system 301 is shown in a disassembled state, wherein the gas analyzer assembly 312, including the ionization chamber 320, channel 341 and gas analyzer 380, are removed from the gas analyzer chamber 310. The system 301 is shown with mounting hardware that may be integral to the system 301 but not shown in FIG. 3B, including a flange 384 at the outer perimeter of the right side of the ionization source pump 360, which accommodates bolts or another mechanism to securely fasten the ionization source pump 360 to the gas analyzer chamber 310 and encompass the opening 324. Further, the ionization chamber 320 may include a connector 386 (e.g., a ceramic coupling) at the opening at the end of the chamber 320 for contacting the wall of the gas analyzer chamber 310. Alternatively, the connector 386 may be mounted at the opening 324, rather than on the ionization chamber 320. To secure the gas analyzer assembly 312 to the gas analyzer chamber 310, a flange 382 may be applied to the right wall of the gas analyzer 380, and may accommodate bolts or another fastening mechanism to join the gas analyzer 380 and the right edge of the gas analyzer chamber 310.

FIG. 4B illustrates the system 301 in an assembled state. Here, the connector 386 may form a seal between the edge of the ionization chamber 320 and the inner wall of the gas analyzer chamber 310 that leaves the opening 324 unobstructed. In addition, the flanges 382, 384 are fastened to secure the gas analyzer assembly 312 and the ionization source pump 360 to the gas analyzer chamber 310, respectively. To remove the gas analyzer 380, the flange 382 may be unfastened and the gas analyzer assembly 312 may be moved rightward, returning the system 301 to the disassembled state as shown in FIG. 4A. Likewise, the flange 384 may be unfastened to allow removal of the ionization source pump 360, leftward.

Figure 5A:
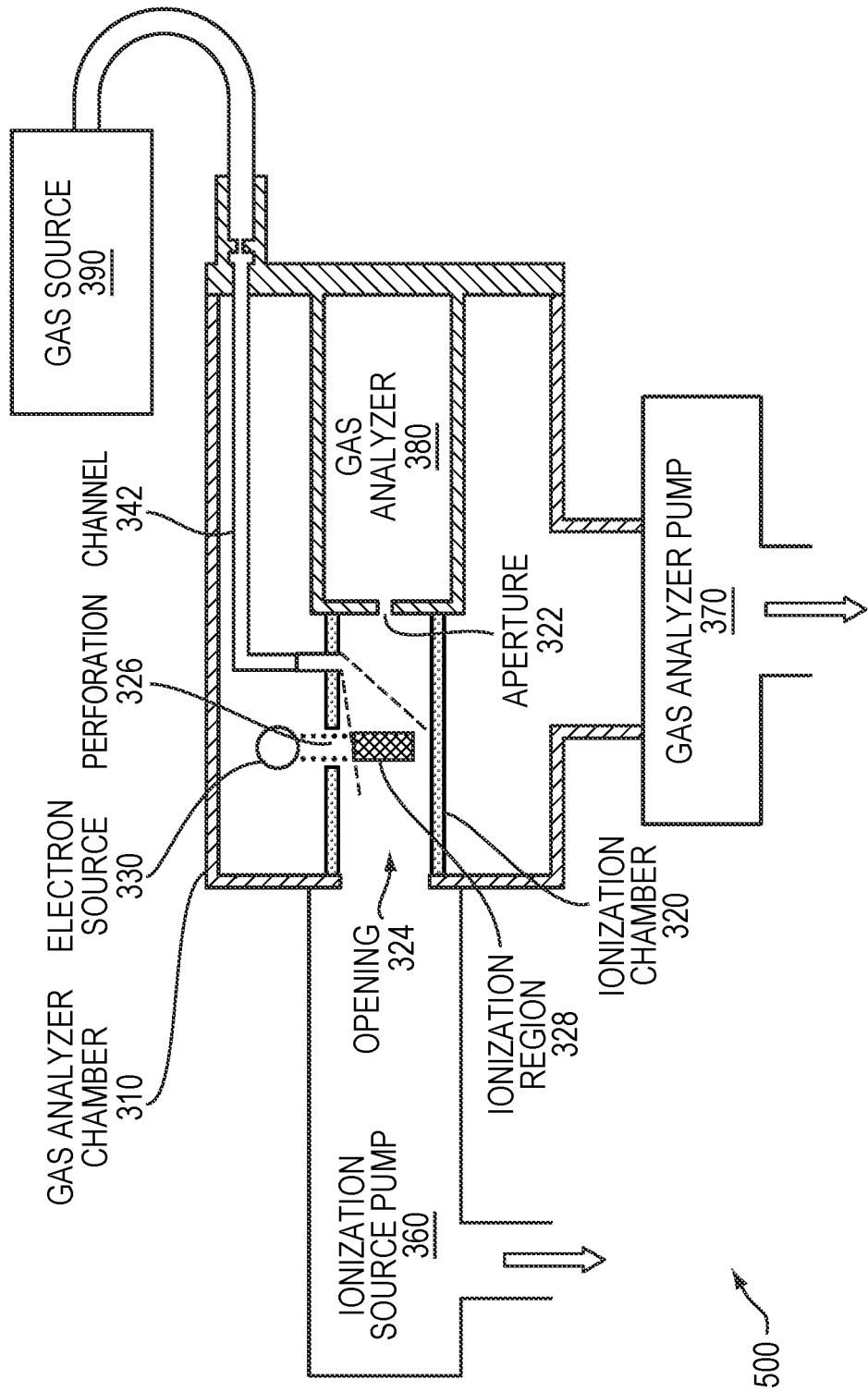
FIGS. 5A-C illustrate gas analyzer systems in further embodiments.
Figure 5B:
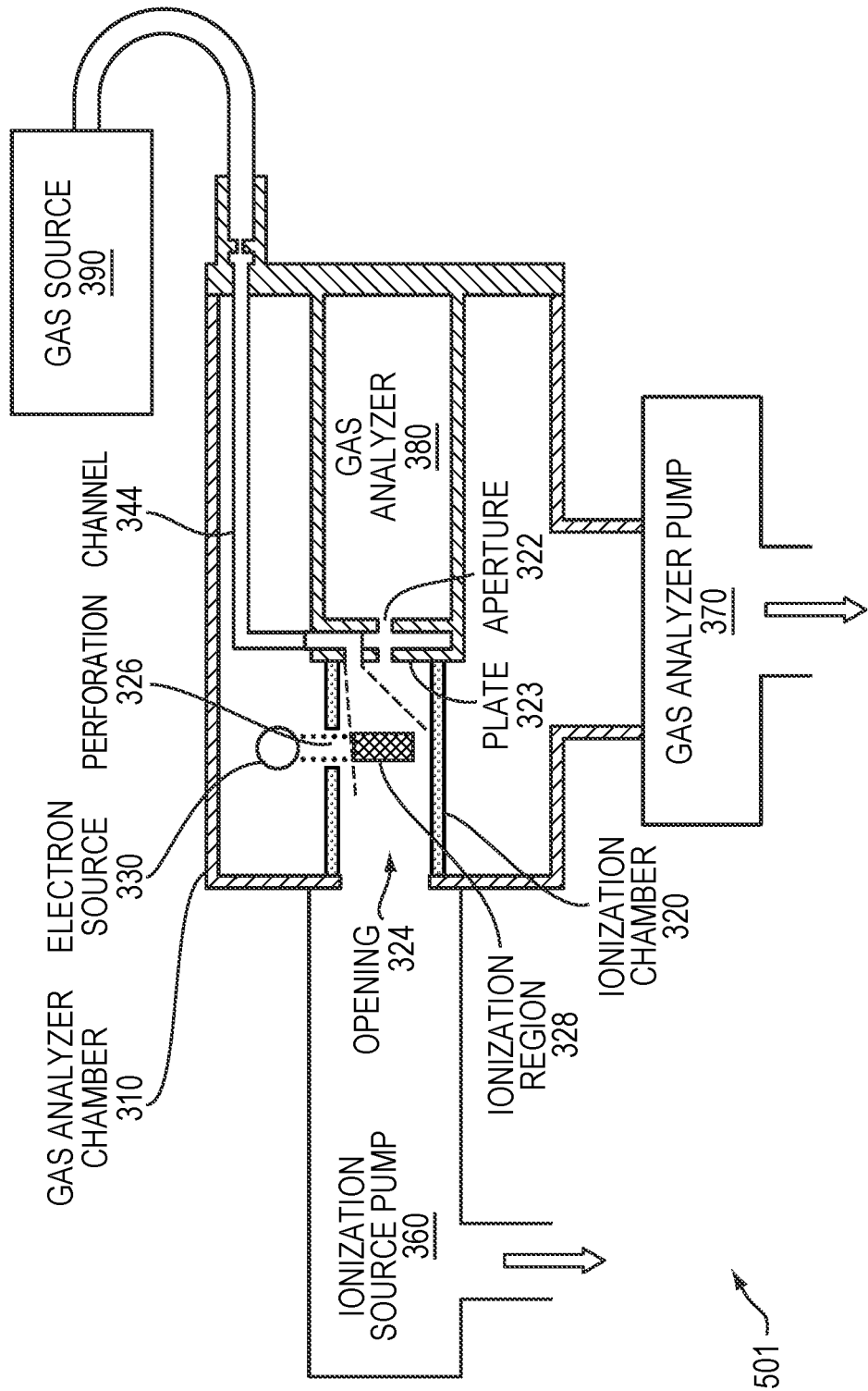
Figure 5C:
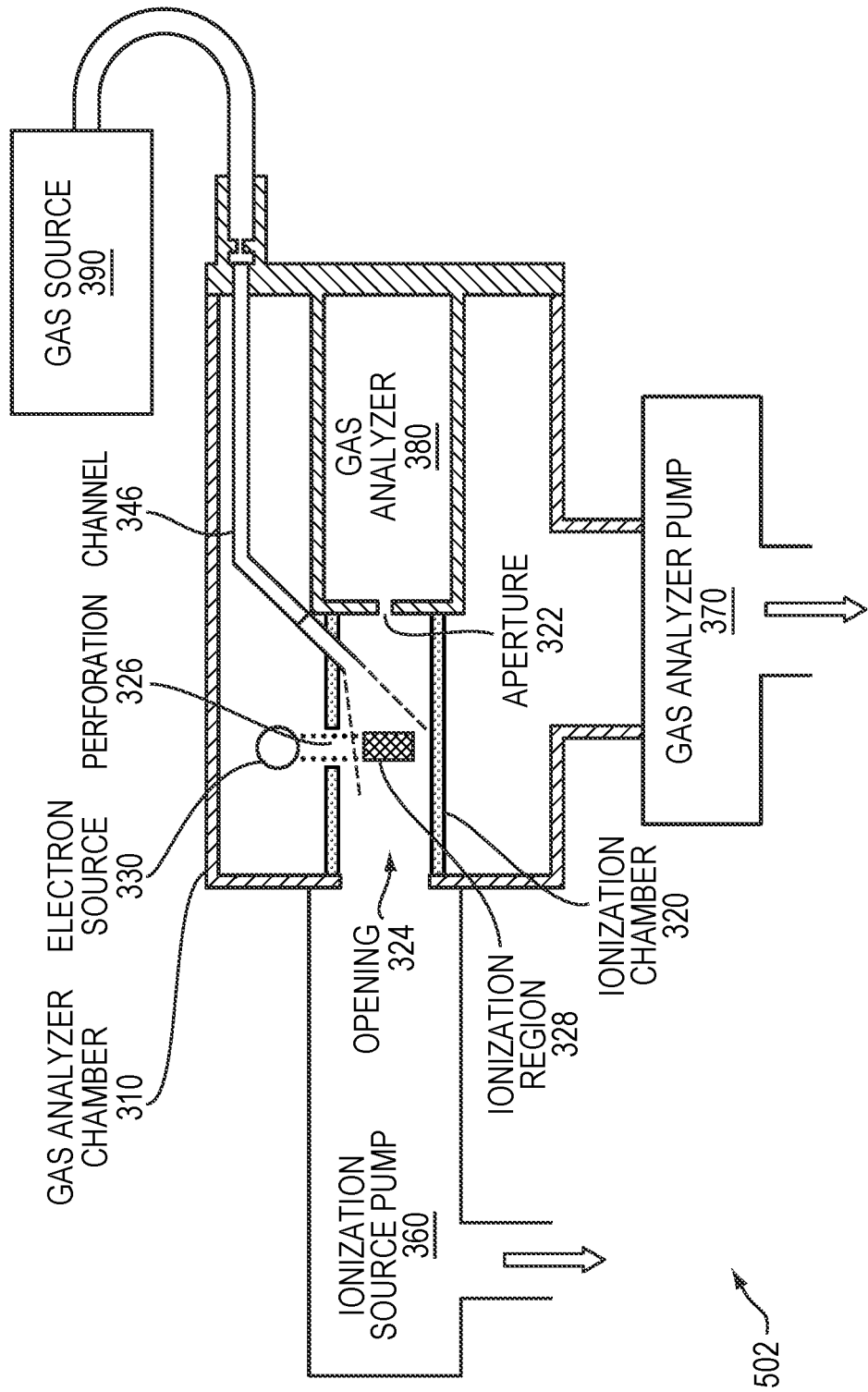

FIGS. 5A-C illustrate gas analyzer systems 500-502 in further embodiments. Each of the systems 500-502 may incorporate some or all of the features of the systems 300, 301 described above, but may depart from the systems 300, 301 in the configuration of the ionization chamber 320, channel 341, and/or gas analyzer 380. In particular, the system 500 of FIG. 5A includes a channel 342 having a right-angle bend with a terminal segment that extends to the ionization chamber 320 in a direction perpendicular to the top surface of the ionization chamber 320. Although the gas may exit the channel 342 in a direction not oriented directly at the ionization region 328, the ionization source pump 360 may draw the gas through the ionization region 328.

In contrast, the system 501 of FIG. 5B includes a channel 344 having two right-angle bends and a vertical segment that extends along a wall of the gas analyzer 380, which is connected to a terminal segment that is oriented into the ionization chamber 320. To secure the position of the channel 344, a plate 323 may be positioned in parallel to the wall of the gas analyzer 380, wherein the channel 344 extends between the plate 323 and the wall. The plate 323 may include an aperture aligned with the aperture 322 into the gas analyzer 380 to permit passage of the ions, as well as a hole to accommodate the terminal segment of the channel 344. The terminal region of the channel 344 may be a passage way bounded by elements of the ionization chamber 320 and the gas analyzer 380, rather than as a discrete tube.

The system 502 of FIG. 5C includes a channel 346 that is oriented comparably to the channel 340 of FIG. 3B, in that the terminal segment intersects the surface of the ionization chamber 320 at a diagonal angle generally oriented toward the ionization region 328. However, the terminal segment of the channel 346 extends into the ionization chamber 320 up to a location adjacent to the ionization region 328 and the path traveled by an electron stream emitted by the electron source 330. By extending the channel 346 into the chamber 320 in this manner, a greater number of gas particles may pass through the ionization region 328, which may potentially provide a higher gas pressure within the ionization region and a greater number of ions generated for measurement by the gas analyzer 380.

Figure 6A:
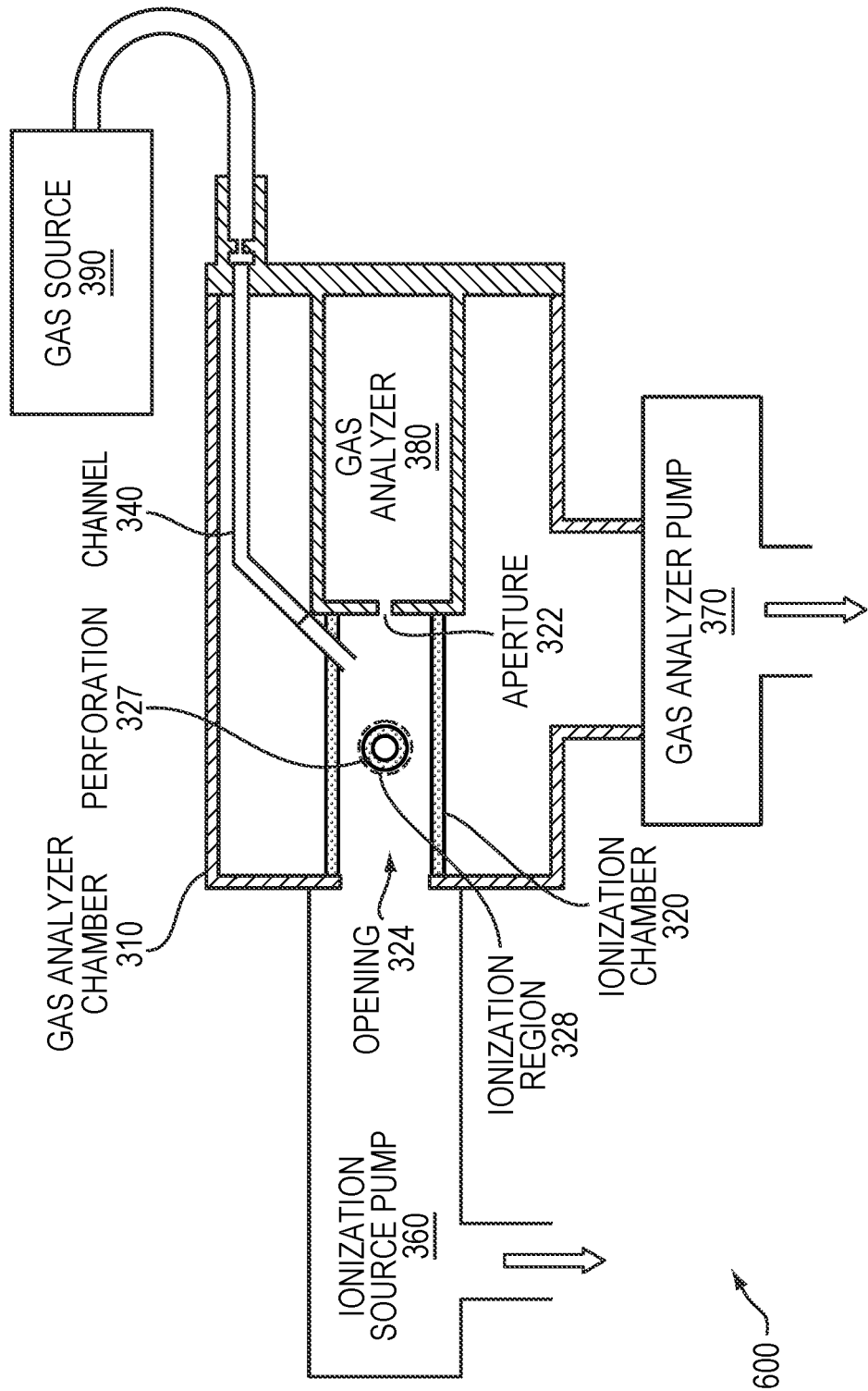
FIGS. 6A-B illustrate a gas analyzer system in a further embodiment.
Figure 6B:
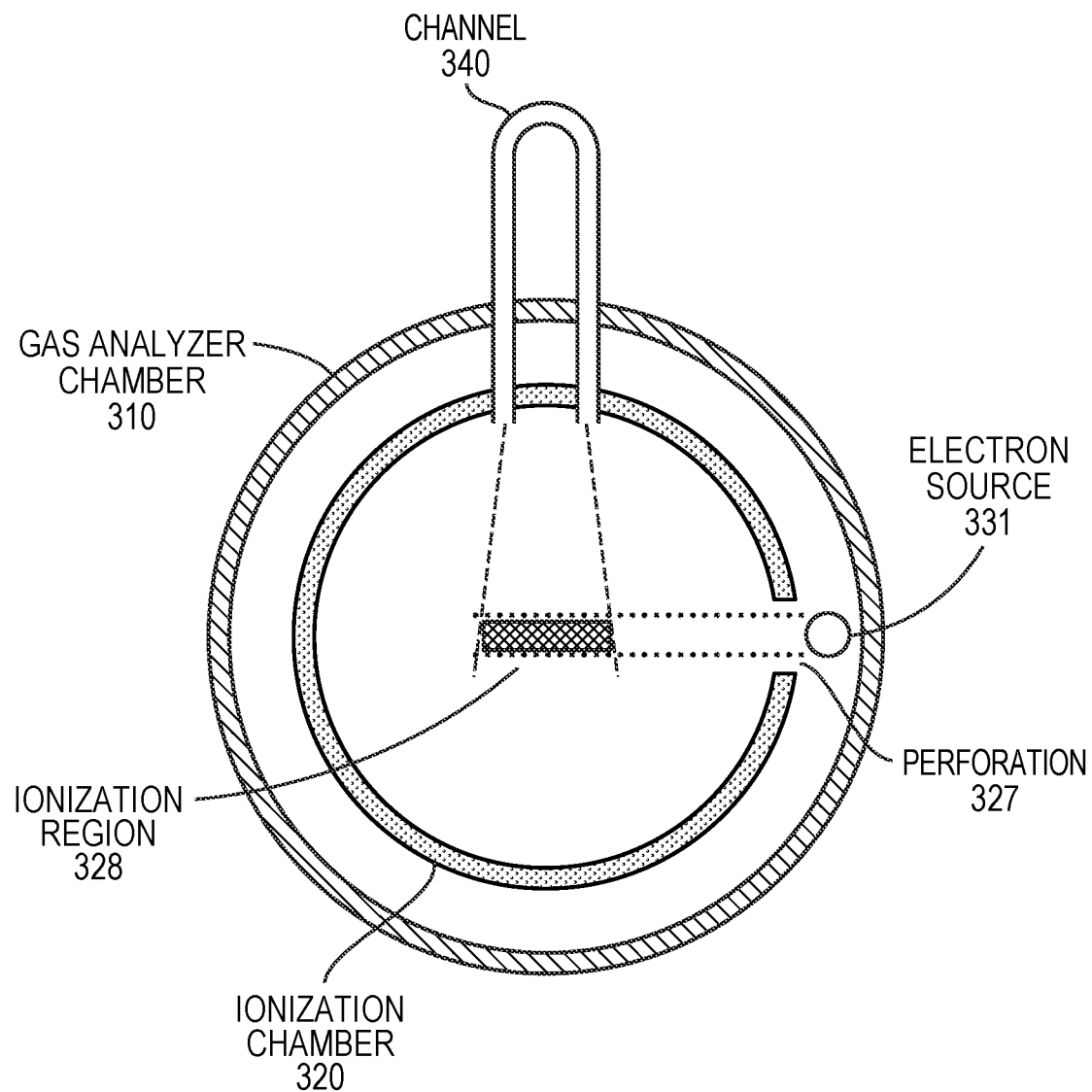

FIGS. 6A-B illustrate a gas analyzer system 600 in a further embodiment. The system 600 may incorporate some or all of the features of the systems 300, 301, 302, 500, 502 described above, but may depart from the system 301 in the configuration of the ion source. In particular, a perforation 327 for permitting passage of electrons may be located at a lateral surface of the ionization chamber 320 as shown in FIG. 6A, that is not aligned adjacent to the channel 340. FIG. 6B is a side view of the gas analyzer chamber 310 and connected components. Here, an electron source 331 is located to the right of the ionization chamber 320, and generates electrons that are directed through the perforation 327 and toward the ionization region 328. Concurrently, the channel 340 directs the gas from above the ionization chamber 320 toward the ionization region 328, where a portion of the gas is charged by the electrons to form ions for measurement by the gas analyzer 380. In further embodiments, the system 600 may implement a channel and ionization chamber configuration of one or more FIGS. 5A-C. Further, the systems 300, 301, 302, 500, 501, 502 may implement multiple perforations to enable passage of electrons into the ionization chamber, as well as multiple electron sources.

Figure 7:
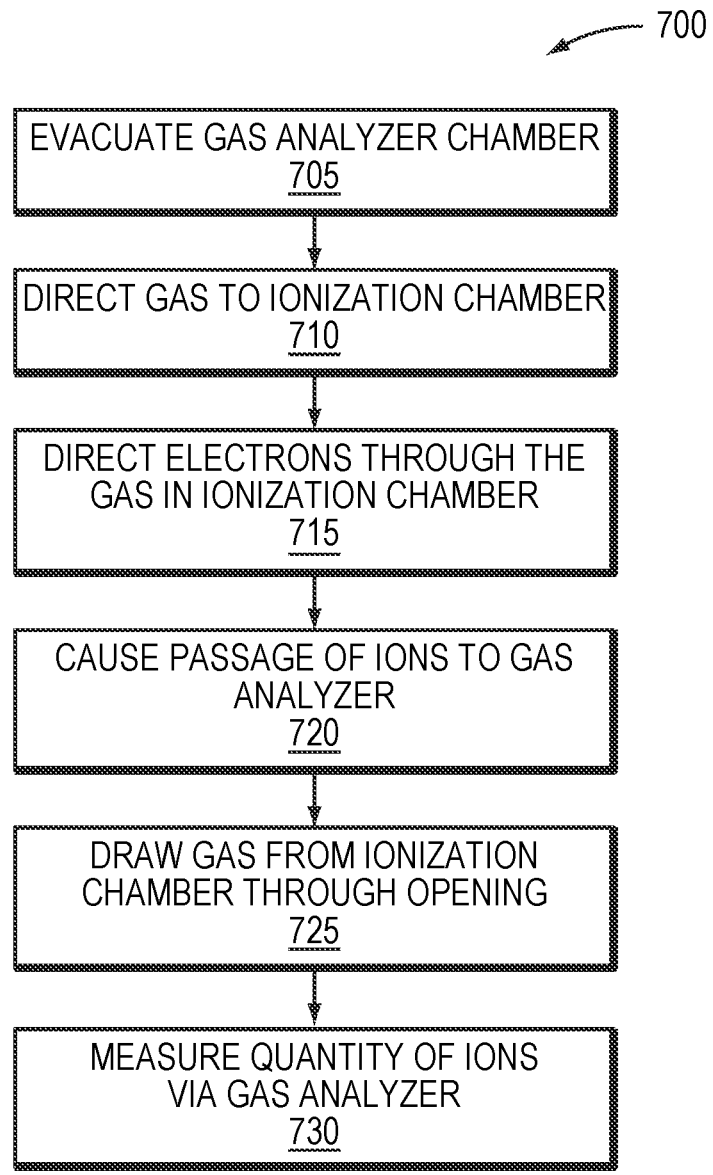
FIG. 7 is a flow diagram of a method of processing and analyzing gas in one embodiment.

FIG. 7 is a flow diagram of a method 700 of processing and analyzing gas in one embodiment. With reference to system 301 in FIG. 3, for example, the gas analyzer chamber 310 may be evacuated via the gas analyzer vacuum pump 370 (705). The channel 341 may direct gas from a gas source 390 to an ionization chamber 320 within the gas analyzer chamber 310, the channel 341 extending to a surface of the ionization chamber 320 (710). Concurrently, the electron source 330 may direct electrons through the gas in the ionization chamber to ionize the gas (715). The ions may be caused (e.g. via an electromagnetic field) to pass from the ionization chamber 320 to the gas analyzer 380 via an aperture 322 at the ionization chamber (720). Gas may then be drawn from the ionization chamber 320 through the opening 324 at the ionization chamber 320 via the ionization source pump 360 (725). The gas analyzer 380 may measure a quantity of ions generated from the gas to determine the quantity of one or more gas species present in the gas (730). The method 700 may be performed by any of the systems described herein.

While example embodiments have been particularly shown and described, it will be understood by those skilled in the art that various changes in form and details may be made therein without departing from the scope of the embodiments encompassed by the appended claims.

What is claimed is:

1. A system for analyzing gas, comprising:
a gas analyzer in a gas analyzer chamber configured to measure a quantity of ions generated from a gas;
a gas analyzer vacuum pump configured to evacuate the gas analyzer chamber;
an ionization source comprising:
an ionization chamber encompassing an ionization region in which particles of the gas are charged to form the ions, including 1) an aperture permitting passage of the ions between the ionization chamber and the gas analyzer chamber, 2) an opening substantially larger than the aperture and positioned away from the aperture, and 3) a perforation through the chamber, at a position between the aperture and the opening, for electrons to enter the ionization region; and an electron source configured to direct electrons into the ionization chamber via the perforation and through the gas in the ionization chamber into the ionization region to ionize the gas;

a channel configured to direct the gas from a gas source into the ionization chamber at a location between the aperture and the ionization region and in a direction extending away from the aperture, the channel extending to a surface of the ionization chamber; and an ionization source vacuum pump in gaseous communication with the ionization chamber via the opening, the ionization source vacuum pump configured to draw gas from the ionization chamber.

2. The system of claim 1, wherein the gas analyzer is removeable axially from the gas analyzer chamber.

3. The system of claim 2, wherein the channel extends axially beside the gas analyzer and is removed axially with the gas analyzer and the ionization chamber.

4. The system of claim 1, wherein the channel extends to the surface of the ionization chamber at a location closer to the aperture than the opening.

5. The system of claim 1, wherein the aperture and the opening are located at opposite ends of the ionization chamber.

6. The system of claim 1, wherein the channel is adapted to direct at least a portion of the gas into the ionization region prior to collision with an interior surface of the ionization chamber.

7. The system of claim 1, wherein the channel includes a terminal segment that is oriented towards the ionization region.

8. The system of claim 7, wherein the terminal segment extends into the ionization chamber to a location adjacent to an electron stream from the electron source.

9. The system of claim 1, wherein the ionization chamber is configured to maintain a gas pressure higher than a gas pressure of the gas analyzer chamber.

10. The system of claim 9, wherein the ionization chamber is configured to contain the gas at a pressure below $5 \times 10^{-2}$ Torr, and wherein the gas analyzer chamber is configured to contain the gas at a pressure below $1 \times 10^{-4}$ Torr.

11. The system of claim 1, wherein the channel extends to the surface of the ionization chamber at a location between the perforation for the electrons and the aperture.

12. The system of claim 1, wherein the gas analyzer is a quadrupole mass analyzer (QMA).

13. A system for analyzing gas, comprising:
an ionization source comprising:
an ionization chamber encompassing an ionization region in which particles of the gas are charged to form ions, including 1) an aperture permitting passage of the ions from the ionization chamber to an evacuated gas analyzer chamber and 2) an opening substantially larger than the aperture and positioned away from the aperture, and 3) a perforation through the chamber, at a position between the aperture and the opening, for electrons to enter the ionization region;

a channel configured to direct the gas from a gas source to the ionization chamber at a location between the aperture and the ionization region and in a direction extending away from the aperture, the channel extending through a surface of the ionization chamber, and an electron source configured to direct electrons into the ionization chamber via the perforation and through the gas in the ionization chamber to ionize the gas, the ionization chamber encompassing an ionization region in which particles of the gas form the ions; and an ionization source vacuum pump in gaseous communication with the ionization chamber via the opening, the ionization source vacuum pump configured to draw gas from the ionization chamber.

14. The system of claim 13, wherein the channel and ionization chamber are removable axially from the gas analyzer chamber.

15. The system of claim 14, wherein the channel extends to the surface of the ionization chamber at a location closer to the aperture than the opening.

16. The system of claim 13, wherein the aperture and the opening are located at opposite ends of the ionization chamber.

17. The system of claim 13, wherein the channel is adapted to direct at least a portion of the gas into the ionization region prior to collision with an interior surface of the ionization chamber.

18. The system of claim 13, wherein the channel includes a terminal segment that is oriented towards the ionization region.

19. The system of claim 18, wherein the terminal segment extends into the ionization chamber to a location adjacent to an electron stream from the electron source.

20. A method of analyzing gas, comprising:
evacuating a gas analyzer chamber via a gas analyzer vacuum pump;
directing, via a channel, gas from a gas source to an ionization chamber within the gas analyzer chamber, the channel extending to a surface of the ionization chamber;
directing electrons through the gas in the ionization chamber to ionize the gas, the ionization chamber encompassing an ionization region in which particles of the gas are charged to form ions;
causing passage of the ions from the ionization chamber to a gas analyzer in the gas analyzer chamber via an aperture at the ionization chamber; and
drawing gas from the ionization chamber through an opening at the ionization chamber via an ionization source vacuum pump, the opening being substantially larger than the aperture and positioned away from the aperture,
wherein the channel extends to the surface of the ionization chamber at a location between the aperture and the ionization region, and
wherein directing the gas includes directing the gas a direction extending away from the aperture.

21. The method of claim 20, further comprising measuring a quantity of ions generated from a gas via a gas analyzer.

22. A system for analyzing gas, comprising:
a gas analyzer in a gas analyzer chamber configured to measure a quantity of ions generated from a gas;
a gas analyzer vacuum pump configured to evacuate the gas analyzer chamber;
an ionization source comprising:
an ionization chamber encompassing an ionization region in which particles of the gas are charged to form the ions, including 1) an aperture permitting passage of the ions between the ionization chamber and the gas analyzer chamber, 2) an opening substantially larger than the aperture and positioned away from the aperture, and 3) a perforation through the ionization chamber, at a position between the aperture and the opening, for electrons to enter the ionization region; and an electron source configured to direct electrons into the ionization chamber via the perforation and through the gas in the ionization chamber into the ionization region to ionize the gas;

a channel configured to direct the gas from a gas source into the ionization chamber, the channel having a terminal segment located in the ionization chamber at a location closer to the aperture than the opening; and an ionization source vacuum pump in gaseous communication with the ionization chamber via the opening, the ionization source vacuum pump configured to draw gas from the ionization chamber.

23. The system of claim 22, wherein the terminal segment is located between the perforation for the electrons and the aperture.

\* \* \* \* \*